(12) United States Patent
Levi et al.

(10) Patent No.: US 9,072,521 B2
(45) Date of Patent: Jul. 7, 2015

(54) NON-INVASIVE DEVICE FOR TREATING BODY TISSUE

(75) Inventors: BenZion Levi, Kibbutz Habonim (IL); Moshe Mizrahy, Tel Aviv (IL)

(73) Assignee: HOME SKINOVATIONS LTD., Yokneam (IL)

( * ) Notice: Subject to any disclaimer, the term of this patent is extended or adjusted under 35 U.S.C. 154(b) by 0 days.

(21) Appl. No.: 13/491,616

(22) Filed: Jun. 8, 2012

(65) Prior Publication Data

US 2013/0331913 A1    Dec. 12, 2013

(51) Int. Cl.
| | |
|---|---|
| *A61N 5/06* | (2006.01) |
| *A61B 18/18* | (2006.01) |
| *A61F 7/12* | (2006.01) |
| *A61B 18/14* | (2006.01) |
| *A61B 18/20* | (2006.01) |
| *A61B 18/00* | (2006.01) |
| *A61B 18/08* | (2006.01) |

(52) U.S. Cl.
CPC .............. *A61B 18/14* (2013.01); *A61B 18/18* (2013.01); *A61N 5/062* (2013.01); *A61N 2005/0652* (2013.01); *A61B 2018/00452* (2013.01); *A61B 18/1815* (2013.01); *A61B 18/08* (2013.01); *A61B 18/203* (2013.01); *A61B 2018/00791* (2013.01); *A61B 2018/00994* (2013.01); *A61B 2018/1807* (2013.01)

(58) Field of Classification Search
CPC ........... A61N 5/062; A61N 2005/0652; A61B 18/18; A61B 18/1815; A61B 18/203; A61B 2018/00452
USPC ......................................... 607/88, 101; 606/9
See application file for complete search history.

(56) References Cited

U.S. PATENT DOCUMENTS

| | | | | |
|---|---|---|---|---|
| 5,196,759 | A * | 3/1993 | Parham et al. ................. | 313/112 |
| 6,692,490 | B1 * | 2/2004 | Edwards ........................ | 606/41 |
| 6,702,808 | B1 | 3/2004 | Kreindel | |
| 2003/0153961 | A1 * | 8/2003 | Babaev .......................... | 607/89 |
| 2006/0173518 | A1 | 8/2006 | Kreindel | |
| 2008/0183251 | A1 * | 7/2008 | Azar et al. .................... | 607/101 |
| 2009/0259219 | A1 * | 10/2009 | Ottini ............................. | 606/9 |
| 2010/0016761 | A1 | 1/2010 | Rosenberg | |

(Continued)

FOREIGN PATENT DOCUMENTS

| | | |
|---|---|---|
| WO | 2009/104178 | 8/2009 |
| WO | WO 2010029536 A2 * | 3/2010 |
| WO | 2013/076714 | 5/2013 |

OTHER PUBLICATIONS

PCT Written Opinion PCT/US2013/044428, Dec. 11, 2013.

*Primary Examiner* — William Thomson
*Assistant Examiner* — Sebastian X Lukjan
(74) *Attorney, Agent, or Firm* — Dekel Patent Ltd.; David Klein

(57) ABSTRACT

A device including a combined energy applicator including RF electrodes spaced apart that are operable in a bipolar mode for application of RF energy, one or more thermal energy elements for application of thermal energy, and one or more optical energy elements for application of light energy, a temperature sensor assembled in the combined energy applicator for detecting a temperature generated to a skin of a patient, and control circuitry programmed to select which of the RF energy, optical energy and thermal energy is applied to the skin, the temperature sensor being operative in a control loop with the control circuitry to control the energies in accordance with sensed feedback temperature.

15 Claims, 3 Drawing Sheets

(56) References Cited

U.S. PATENT DOCUMENTS

| | | |
|---|---|---|
| 2010/0211055 A1 | 8/2010 | Eckhouse |
| 2011/0112520 A1 | 5/2011 | Michael |
| 2011/0264173 A1* | 10/2011 | Flyash et al. ............ 607/62 |
| 2012/0310232 A1* | 12/2012 | Erez ..................... 606/33 |

* cited by examiner

NON-INVASIVE DEVICE FOR TREATING BODY TISSUE

FIELD OF THE INVENTION

The present invention relates to non-invasive devices and method for treating body tissue, and particularly a device that combines RF (radiofrequency) energy, optical energy and thermal energy for external application on the skin of a patient, such as for treatment of skin (e.g., wrinkle removal skin rejuvenation, etc.), or sub-dermal treatment of body fat, cellulite, skin tightening etc.

BACKGROUND OF THE INVENTION

Treatment of the upper layer of the skin, epidermis and dermis is performed in order to achieve younger and nice appearance of the skin. Light therapy is a very effective tool in addressing a variety of lesions in the skin such as pigmented and vascular lesions, wrinkles and fine lines. Both laser light and incoherent light energy have been suggested for use, wherein pulsed optical energy heats the selected lesion without damaging the surrounding tissue.

Cellulite is a well-known skin condition commonly found on the thighs, hips and buttocks. Cellulite has the effect of producing a dimpled appearance on the surface of the skin. In the human body, subcutaneous fat is contained beneath the skin by a network of tissue called the fibrous septae. When irregularities are present in the structure of the fibrous septae, lobules of fat can protrude into the dermis between anchor points of the septae, creating the appearance of cellulite.

Excess adipose tissue is responsible for different problems as obesity, cellulite, loose skin, and wrinkles. By reducing the size of fat cells, the appearance of the outer layer of the skin can be improved. The reduction of adipose tissue in the sub-dermal layer can help in weight reduction, cellulite reduction, loose skin reduction, deep wrinkle reduction and body re-contouring. Reduction of the fat content may also cause skin tightening. Wrinkles are created in skin due to the breakage of collagen fibers and to the penetration of fat into the dermal layer of the skin. RF energy has been used to reduce adipose tissue in the sub-dermal layer.

SUMMARY OF THE INVENTION

The present invention seeks to provide non-invasive devices and methods that combine RF energy, optical energy and thermal energy for external application on the skin of a patient, as is described more in detail hereinbelow.

In one embodiment, the device combines three energies: bipolar RF energy, such as for deep sub-dermal heating, collagen tightening and wrinkles; thermal energy, such as for superficial treatment of the epidermis, skin texture and reduction of pores; and optical energy which can penetrate (e.g., up to 1.8 mm) for superficial treatment of pigmented lesions, fine lines, wrinkles and rebuilt collagen structure. The device can work with either all energies together or by a suitable combination thereof that alternates between some or all of the energies. Combining the three energies in one device enables treating all layers of the skin from the epidermis to sub-dermal fat simultaneously with a uniform temperature (as deep as 5 mm for facial skin and 12 mm for body skin, for example). Such treatment is optimal for skin rejuvenation of the face, treatment of wrinkles through tightening, mainly with the bipolar RF energy, fine lines, skin texture, pigmented lesions and superficial vascular with heating and light.

In another embodiment, the device may be used for treatment of cellulite and skin tightening of the body, with deeper sub-dermal heating.

Each embodiment also includes a skin temperature sensor to detect the skin temperature constantly which enables adjustment of the energy accordingly in order to prevent any possible adverse effects.

In one embodiment, the control circuitry is used to select which of the RF energy, optical energy and thermal energy is applied to the skin, the temperature sensor being operative in a control loop with the control circuitry to control the energies in accordance with sensed feedback temperature. For example, RF energy and thermal energy may be applied over a first time duration, and thermal energy and optical energy over a second time duration. Alternatively, RF energy, thermal energy and optical energy may be applied over a first time duration, and thermal energy and optical energy over a second time duration. As another alternative, RF energy and thermal energy may be applied over a first time duration, and RF energy, thermal energy and optical energy over a second time duration. There are many more possibilities and these examples are not limiting.

BRIEF DESCRIPTION OF THE DRAWINGS

These and additional constructional features and advantages of the invention will be more readily understood in the light of the ensuing description of embodiments thereof, given by way of example only, with reference to the accompanying drawings wherein.

DETAILED DESCRIPTION OF EMBODIMENTS

Figure 1:
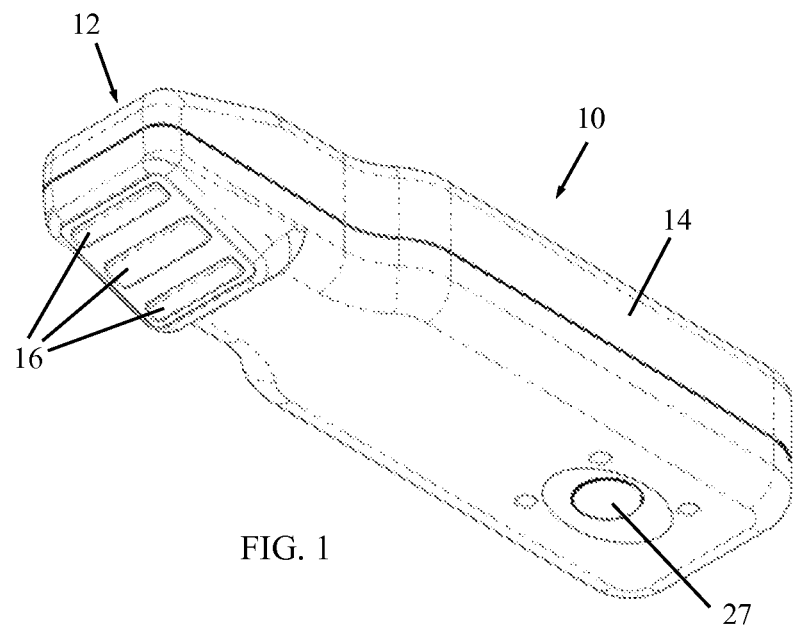
FIG. 1 is a simplified pictorial illustration of a device for treating skin with any combination of three modalities (RF energy, optical energy and thermal energy), constructed and operative in accordance with an embodiment of the present invention.
Figure 3A:
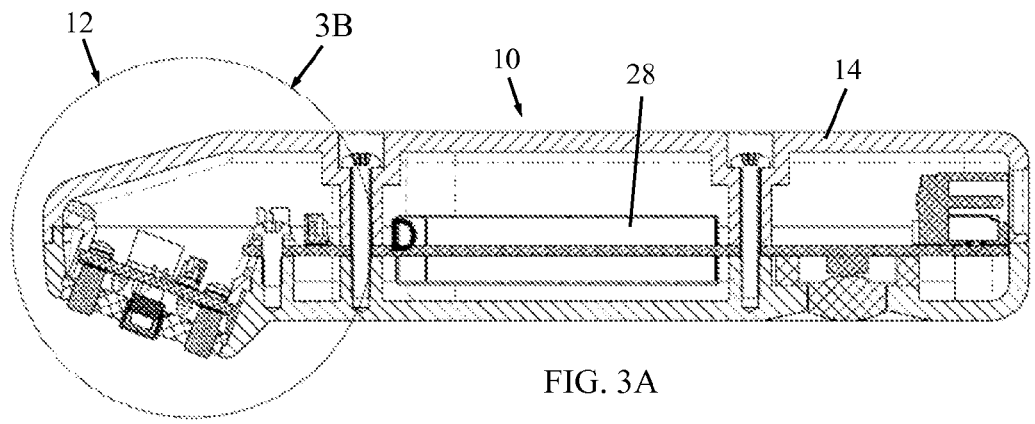
FIGS. 3A-3B are simplified sectional illustrations of the device of FIG. 1, showing internal components thereof, FIG. 3B being an enlarged illustration of the device treatment head.
Figure 3B:
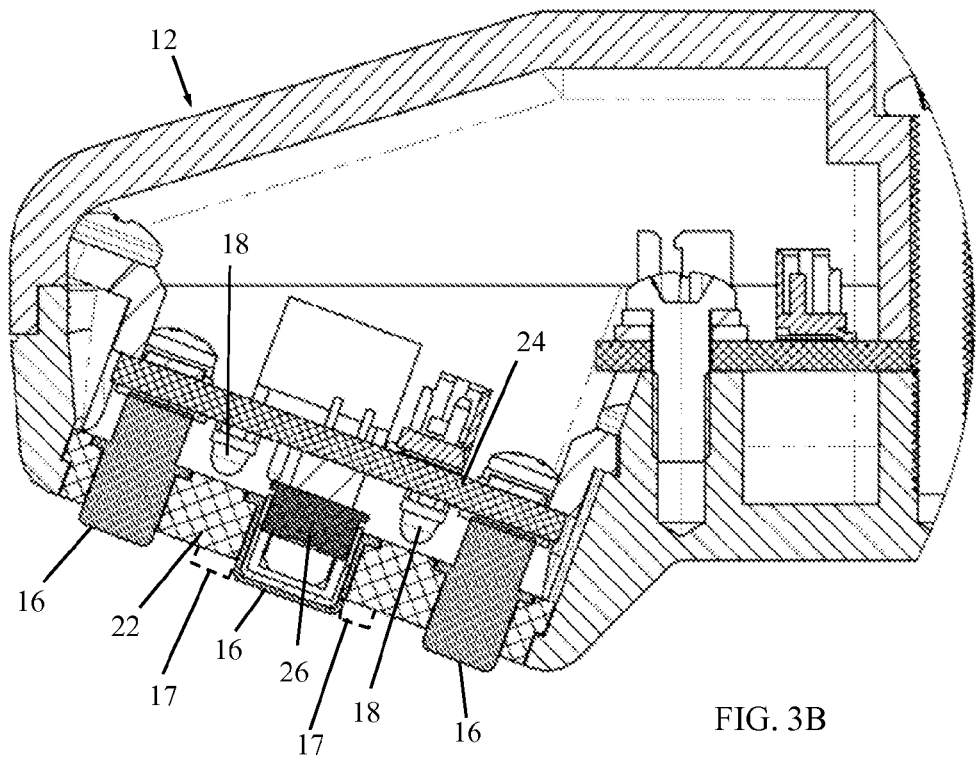

Reference is now made to FIG. 1, and particularly to FIGS. 3A-3B, which illustrate a device 10 for treating skin with any combination of three modalities (RF energy, optical energy and thermal energy), constructed and operative in accordance with a non-limiting embodiment of the present invention.

Device 10 includes a combined energy applicator 12 (also referred to as a treatment head 12), which extends axially from a grasping portion 14. The combined energy applicator 12 includes RF electrodes 16, such as but not limited to, three electrodes spaced apart that operate in a bipolar mode. For example, the two outer electrodes may be negative and the central electrode positive. Without limitation, operating parameters for the RF electrodes 16 may be an RF frequency of 1 MHz (sinusoidal waveform), with an RF treatment power of 25 W maximum. The RF frequency can vary (without limitation, in the range of 0.5-3 MHz) and the power can vary (without limitation, in the range of 1-25 W); the invention is not limited to these values. The bipolar RF energy is particularly effective for deep sub-dermal heating, collagen tightening and wrinkles, for example.

The same electrodes 16 are also utilized for application of thermal energy. In this mode of operation, one or more electrodes are heated with electrical current (typically DC but could also be AC) and transfer heat to the epidermis by thermal radiation (or infrared radiation), convection or conduction or a combination thereof. Alternatively, the electrodes may be heated by RF energy (monopolar or bipolar or a combination thereof). As another alternative, the electrodes may be heated by a combination of electrical current and RF energy. In yet another alternative, there may be a non-electrode heat source 17 (shown in broken lines in FIG. 3B), such as but not limited to, an infrared heater, a halogen lamp, electrical, optical and chemical sources of heat and any combination thereof.

Without limitation, operating parameters may be a heat power of 5 W maximum, and an electrode temperature cut off at 39° C. The treatment temperature may be 41° C. The invention is not limited to these values. The application of thermal energy is particularly effective for superficial treatment of the epidermis, skin texture and reduction of pores, for example.

The combined energy applicator 12 includes one or more optical energy elements 18, which emit either coherent or incoherent light. In one preferred embodiment, the optical energy elements 18 are LEDs, but other elements may be used, e.g., incandescent lamp, laser (such as laser diode), or gas filled lamp. The light emitted by optical energy elements 18 may be continuous or pulsed. For example, without limitation, the light wavelength may be 645 nm (or in the range of about 450-10,000 nm) either CW (continuous wave) or with a pulse width of about 10 msec 1 sec, and power 100 mW maximum (alternatively, an energy fluence of about 0.5-100 J/cm$^2$). The light may be delivered as a single pulse at one place on the skin or a series of pulses at one place on the skin before moving to other treatment sites on the skin. LED optical energy can penetrate up to 1.8 mm for superficial treatment of pigmented lesions and fine lines.

The RF electrodes 16 may be mounted in and pass through a skin interface element 22. The optical energy elements 18 may be mounted on a substrate 24 behind skin interface element 22. Substrate 24 may also support electrodes 16. Skin interface element 22 is preferably light transparent at least in the areas where light energy passes from optical energy elements 18. Skin interface element 22 may be made, for example, from polycarbonate or other transparent material. Skin interface element 22 may be applied directly to the skin or alternatively through conducting media, such as gel, cream and the like.

A temperature sensor 26 is assembled in combined energy applicator 12, such as in a portion of skin interface element 22 near the middle electrode 16, for detecting the skin temperature. In the illustrated embodiment, temperature sensor 26 is an infrared (IR) temperature element. The invention is not limited to this, and temperature sensor 26 may be alternatively a thermistor (positive or negative coefficient), thermotransistor, thermocouple, and others. Temperature sensor 26 may operate in a control loop with control circuitry 28 (FIG. 3A) to control or cut off energy in accordance with the feedback temperature sensed. The control circuitry 28 is programmed to select which of the three types of energy (RF energy, optical energy and thermal energy) are applied to the skin. An on-off switch 27 (FIG. 1) and other control switches or displays may be provided.

Accordingly, device 10 can apply all three energies together, or by adjustment of the software of control circuitry 28, can alternate between the three energies. Combining the three energies in one device enables treating all layers of the skin, from the epidermis up to and including sub-dermal fat simultaneously as deep as 5 mm, while creating a uniform temperature of 41-42° C. Such treatment is optimal for skin rejuvenation of the face, treatment of wrinkles through tightening, mainly with the bipolar RF energy, fine lines, skin texture, pigmented lesions and superficial vascular with the heating and optical energy. The skin temperature control sensor 26 provides a safety feature to eliminate any possibility of adverse effects.

As stated above, the software of control circuitry 28 can automatically control the energy cycles and alternating between the energy types. Some non-limiting examples include 30 seconds applying RF and IR heating, and then 30 seconds of IR heating and optical energy, or 45 seconds of RF and heating and only 15 seconds of IR and optical, or applying constantly all energies together. There are many possible combinations for applying the energy through the software. Fine-tuning can be done according to stored patient history or in accordance with clinical studies.

Figure 2:
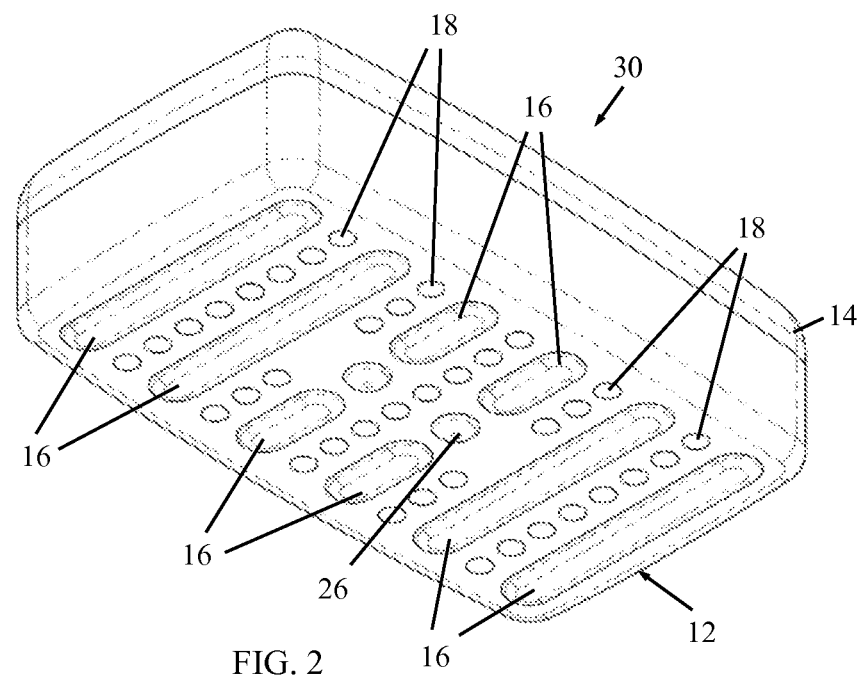
FIG. 2 is a simplified pictorial illustration of a device for treating skin with any combination of three modalities (RF energy, optical energy and thermal energy), constructed and operative in accordance with another embodiment of the present invention.
Figure 4A:
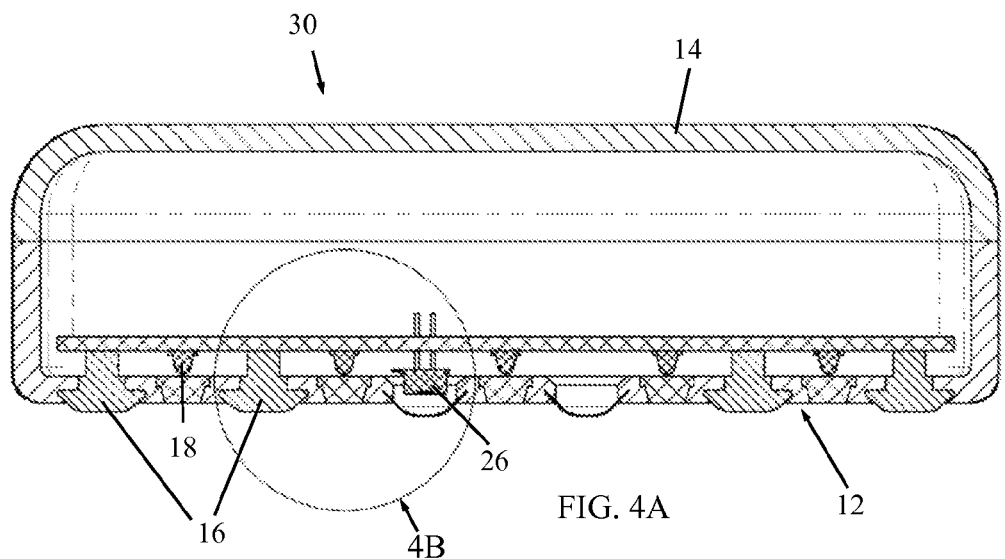
FIGS. 4A-4B are simplified sectional illustrations of the device of FIG. 2, showing internal components thereof, FIG. 4B being an enlarged illustration of the device treatment head.
Figure 4B:
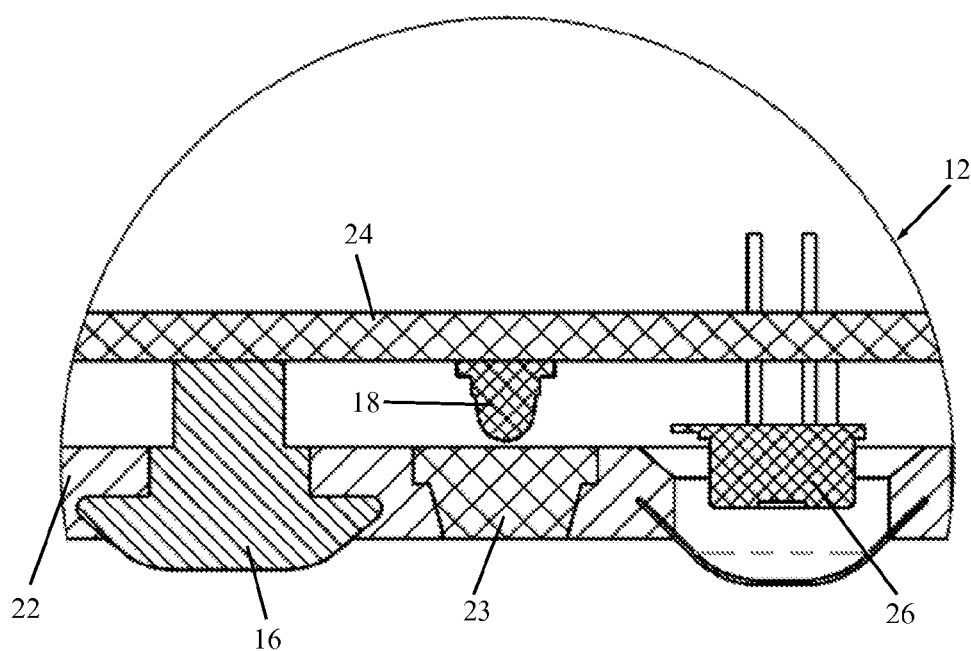

Reference is now made to FIG. 2, and particularly to FIGS. 4A-4B, which illustrate a device 30 for treating skin with any combination of three modalities (RF energy, optical energy and thermal energy), constructed and operative in accordance with another non-limiting embodiment of the present invention.

Device 30 is similar to device 10, with like elements being designated by like numerals. In the illustrated embodiment, device 30 includes 6 electrodes 16 (as opposed to just 3 in device 10), and the distance between the RF electrodes 16 is wider than in device 10. Because of this wider distance, the sub-dermal heating is deeper (e.g., as deep as 10 mm), which makes device 30 effective for treatment of deeper body tissues, such as or treatment of cellulite and skin tightening of the body.

In the illustrated embodiment, device 30 includes 5 rows of optical energy elements 18. The two inner rows of electrodes 16 are separated by temperature sensors 26. The grasping portion 14 extends directly away from combined energy applicator 12, as opposed to axially away in device 10. Skin interface element 22 is light transparent at least in areas 23 where light energy passes from optical energy elements 18, and may be made of a different material (e.g., a thermally conducting or insulating material) in areas where the light energy does not pass through.

Operating parameters of device 30 for the RF electrodes 16 may be, without limitation, RF frequency of 1 MHz (sinusoidal waveform), with an RF treatment power of 25 W maximum (as opposed to 15 for device 10); the invention is not limited to these values. Without limitation, the thermal operating parameters may be a heat power of 10 W maximum (as opposed to 5 for device 10), and the electrode temperature cut off may be 39° C. The treatment temperature may be 41° C. Without limitation, the light wavelength may be 630 nm and power 400 mW maximum (as opposed to 100 for device 10).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method comprising:
applying energy towards a skin with a combined energy applicator that comprises RF electrodes spaced apart that are operable in a bipolar mode for application of RF energy, one or more thermal energy elements for application of thermal energy, and one or more optical energy elements for application of light energy, and a temperature sensor assembled in said combined energy applicator for detecting patient skin temperature; and using control circuitry programmed to select which of the RF energy, optical energy and thermal energy is applied to the skin, said temperature sensor being operative in a control loop with said control circuitry to control the energies in accordance with sensed feedback temperature and using said control circuitry to switch between application of the RF energy, the optical energy and the thermal energy for different periods of time independent of the feedback temperature, and comprising applying RF energy, to cause deep sub-dermal heating, and thermal energy, to cause superficial treatment of epidermis, over a first time duration, and thermal energy, to cause superficial treatment of epidermis, and optical energy, to penetrate up to 1.8 mm into the skin, over a second time duration.

2. A method comprising:
applying energy towards a skin with a combined energy applicator that comprises RF electrodes spaced apart that are operable in a bipolar mode for application of RF energy, one or more thermal energy elements for application of thermal energy, and one or more optical energy elements for application of light energy, and a temperature sensor assembled in said combined energy applicator for detecting patient skin temperature; and using control circuitry programmed to select which of the RF energy, optical energy and thermal energy is applied to the skin, said temperature sensor being operative in a control loop with said control circuitry to control the energies in accordance with sensed feedback temperature and using said control circuitry to switch between application of the RF energy, the optical energy and the thermal energy for different periods of time independent of the feedback temperature, and comprising applying RF energy, to cause deep sub-dermal heating, thermal energy, to cause superficial treatment of epidermis, and optical energy, to penetrate up to 1.8 mm into the skin, over a first time duration, and thermal energy, to cause superficial treatment of epidermis, and optical energy, to penetrate up to 1.8 mm into the skin, over a second time duration.

3. A method comprising:
applying energy towards a skin with a combined energy applicator that comprises RF electrodes spaced apart that are operable in a bipolar mode for application of RF energy, one or more thermal energy elements for application of thermal energy, and one or more optical energy elements for application of light energy, and a temperature sensor assembled in said combined energy applicator for detecting patient skin temperature; and using control circuitry programmed to select which of the RF energy, optical energy and thermal energy is applied to the skin, said temperature sensor being operative in a control loop with said control circuitry to control the energies in accordance with sensed feedback temperature and using said control circuitry to switch between application of the RF energy, the optical energy and the thermal energy for different periods of time independent of the feedback temperature, and comprising applying RF energy, to cause deep sub-dermal heating, and thermal energy, to cause superficial treatment of epidermis, over a first time duration, and RF energy, to cause deep sub-dermal heating, thermal energy, to cause superficial treatment of epidermis, and optical energy, to penetrate up to 1.8 mm into the skin, over a second time duration.

4. The method according to claim 1, comprising using the control circuitry to treat all layers of the skin from epidermis to sub-dermal fat with a uniform temperature.

5. The method according to claim 2, comprising using the control circuitry to treat all layers of the skin from epidermis to sub-dermal fat with a uniform temperature.

6. The method according to claim 3, comprising using the control circuitry to treat all layers of the skin from epidermis to sub-dermal fat with a uniform temperature.

7. The method according to claim 1, comprising heating said RF electrodes with electrical current to apply the thermal energy.

8. The method according to claim 2, comprising heating said RF electrodes with electrical current to apply the thermal energy.

9. The method according to claim 3, comprising heating said RF electrodes with electrical current to apply the thermal energy.

10. The method according to claim 1, comprising using a halogen lamp to apply the thermal energy.

11. The method according to claim 2, comprising using a halogen lamp to apply the thermal energy.

12. The method according to claim 3, comprising using a halogen lamp to apply the thermal energy.

13. The method according to claim 1, comprising using an infrared heater to apply the thermal energy.

14. The method according to claim 2, comprising using an infrared heater to apply the thermal energy.

15. The method according to claim 3, comprising using an infrared heater to apply the thermal energy.

* * * * *